(12) United States Patent
Edwards et al.

(10) Patent No.: US 12,714,848 B2
(45) Date of Patent: Aug. 25, 2026

(54) PERCUTANEOUS CIRCULATORY SUPPORT SYSTEM HAVING IMPROVED TORQUE AND BLOOD FLOW

(71) Applicant: Boston Scientific Scimed Inc., Maple Grove, MN (US)

(72) Inventors: Nathan Edwards, Minneapolis, MN (US); Steven R. Larsen, Lino Lakes, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 529 days.

(21) Appl. No.: 17/893,899

(22) Filed: Aug. 23, 2022

(65) Prior Publication Data

US 2023/0063798 A1 Mar. 2, 2023

Related U.S. Application Data

(60) Provisional application No. 63/237,001, filed on Aug. 25, 2021.

(51) Int. Cl.
*A61M 60/865* (2021.01)
*A61M 60/17* (2021.01)
(Continued)

(52) U.S. Cl.
CPC .......... *A61M 60/865* (2021.01); *A61M 60/17* (2021.01); *A61M 60/216* (2021.01); *A61M 60/416* (2021.01)

(58) Field of Classification Search
CPC .. A61M 60/13; A61M 60/414; A61M 60/237; A61M 60/216; A61M 60/865;
(Continued)

(56) References Cited

U.S. PATENT DOCUMENTS 5,527,159 A 6/1996 Bozeman, Jr. et al.
5,692,882 A 12/1997 Bozeman, Jr. et al.
(Continued)

FOREIGN PATENT DOCUMENTS

EP 0847767 B1 2/2005
EP 2301598 B1 7/2017
(Continued)

OTHER PUBLICATIONS

US 9,067,007 B2, 06/2015, Tanner et al. (withdrawn)
(Continued)

*Primary Examiner* — Deborah L Malamud
(74) *Attorney, Agent, or Firm* — Seager, Tufte & Wickhem LLP

(57) ABSTRACT

Various aspects of the present disclosure are directed towards apparatuses, systems, and methods that system for delivering a blood pump. The system may include a blood pump that may include one or more impellers configured to cause blood to flow through the pump. The system may also include one or more guidewires. The guidewires may include one or more proximal sections and one or more distal sections, and the distal sections may have first dimensions and the proximal sections may have second dimensions, and the first dimensions may be greater than the second dimensions. The guidewires may also be tapered, geometrically shaped, have a curved profile, a combination thereof, or other configurations.

14 Claims, 8 Drawing Sheets

(51) Int. Cl.
*A61M 60/216* (2021.01)
*A61M 60/416* (2021.01)

(58) Field of Classification Search
CPC .............. A61M 60/808; A61M 60/221; A61M 60/812; A61M 60/205; A61M 60/523; A61M 60/804; A61M 60/411; A61M 60/88; A61M 25/09; A61M 2205/04; A61M 60/562; A61M 60/90; A61M 2025/1022; A61M 60/00; Y10S 415/90
See application file for complete search history.

(56) References Cited

U.S. PATENT DOCUMENTS

| | | | |
|---|---|---|---|
| 5,947,892 | A | 9/1999 | Benkowski et al. |
| 6,135,729 | A | 10/2000 | Aber |
| 6,139,487 | A | 10/2000 | Siess |
| 6,176,822 | B1 | 1/2001 | Nix et al. |
| 7,841,976 | B2 | 11/2010 | McBride et al. |
| 7,927,068 | B2 | 4/2011 | McBride et al. |
| 7,972,122 | B2 | 7/2011 | Larose et al. |
| 8,376,707 | B2 | 2/2013 | McBride et al. |
| 8,591,393 | B2 | 11/2013 | Walters et al. |
| 8,597,170 | B2 | 12/2013 | Walters et al. |
| 8,684,904 | B2 | 4/2014 | Campbell et al. |
| 8,721,517 | B2 | 5/2014 | Zeng et al. |
| 8,814,776 | B2 | 8/2014 | Hastie et al. |
| 8,992,163 | B2 | 3/2015 | McBride et al. |
| 9,072,825 | B2 | 7/2015 | Pfeffer et al. |
| 9,138,518 | B2 | 9/2015 | Yuen et al. |
| 9,162,017 | B2 | 10/2015 | Evans et al. |
| 9,308,302 | B2 | 4/2016 | Zeng |
| 9,308,304 | B2 | 4/2016 | Peters et al. |
| 9,327,067 | B2 | 5/2016 | Zeng et al. |
| 9,364,592 | B2 | 6/2016 | McBride et al. |
| 9,364,593 | B2 | 6/2016 | McBride et al. |
| 9,381,288 | B2 | 7/2016 | Schenck et al. |
| 9,402,942 | B2 | 8/2016 | Hastie et al. |
| 9,421,311 | B2 | 8/2016 | Tanner et al. |
| 9,446,179 | B2 | 9/2016 | Keenan et al. |
| 9,675,740 | B2 | 6/2017 | Zeng et al. |
| 9,717,833 | B2 | 8/2017 | McBride et al. |
| 9,750,861 | B2 | 9/2017 | Hastie et al. |
| 9,770,543 | B2 | 9/2017 | Tanner et al. |
| 9,814,814 | B2 | 11/2017 | Corbett et al. |
| 9,872,947 | B2 | 1/2018 | Keenan et al. |
| 9,872,948 | B2 | 1/2018 | Siess |
| 9,895,476 | B2 | 2/2018 | Larose et al. |
| 9,907,890 | B2 | 3/2018 | Muller |
| 9,956,332 | B2 | 5/2018 | Larose et al. |
| 9,962,475 | B2 | 5/2018 | Yuen et al. |
| 9,964,115 | B2 | 5/2018 | Scheckel |
| 10,029,037 | B2 | 7/2018 | Muller et al. |
| 10,039,872 | B2 | 8/2018 | Zeng et al. |
| 10,071,192 | B2 | 9/2018 | Zeng |
| 10,086,121 | B2 | 10/2018 | Fitzgerald et al. |
| 10,105,475 | B2 | 10/2018 | Muller |
| 10,117,980 | B2 | 11/2018 | Keenan et al. |
| 10,149,932 | B2 | 12/2018 | McBride et al. |
| 10,215,187 | B2 | 2/2019 | McBride et al. |
| 10,232,099 | B2 | 3/2019 | Peters et al. |
| 10,251,985 | B2 | 4/2019 | Larose et al. |
| 10,251,986 | B2 | 4/2019 | Larose et al. |
| 10,478,539 | B2 | 11/2019 | Pfeffer et al. |
| 10,478,540 | B2 | 11/2019 | Scheckel et al. |
| 10,525,178 | B2 | 1/2020 | Zeng |
| 10,576,192 | B2 | 3/2020 | Muller et al. |
| 10,576,193 | B2 | 3/2020 | Tanner et al. |
| 10,617,808 | B2 | 4/2020 | Hastie et al. |
| 10,709,829 | B2 | 7/2020 | Muller |
| 10,709,830 | B2 | 7/2020 | Tanner et al. |
| 10,737,008 | B2 | 8/2020 | Corbett et al. |
| 10,765,789 | B2 | 9/2020 | Zeng et al. |
| 10,780,208 | B2 | 9/2020 | Siess et al. |
| 10,786,610 | B2 | 9/2020 | Zeng |
| 10,799,624 | B2 | 10/2020 | Pfeffer et al. |
| 10,842,921 | B2 | 11/2020 | Siess et al. |
| 10,864,308 | B2 | 12/2020 | Muller et al. |
| 10,864,309 | B2 | 12/2020 | McBride et al. |
| 10,874,783 | B2 | 12/2020 | Pfeffer et al. |
| 10,894,115 | B2 | 1/2021 | Pfeffer et al. |
| 10,918,773 | B2 | 2/2021 | Guo et al. |
| 10,960,116 | B2 | 3/2021 | Yuen et al. |
| 10,980,927 | B2 | 4/2021 | Pfeffer et al. |
| 11,058,865 | B2 | 7/2021 | Fitzgerald et al. |
| 11,123,539 | B2 | 9/2021 | Pfeffer et al. |
| 11,129,978 | B2 | 9/2021 | Pfeffer et al. |
| 11,167,124 | B2 | 11/2021 | Pfeffer et al. |
| 11,229,786 | B2 | 1/2022 | Zeng et al. |
| 11,235,138 | B2 | 2/2022 | Gross-Hardt et al. |
| 11,253,693 | B2 | 2/2022 | Pfeffer et al. |
| 11,260,213 | B2 | 3/2022 | Zeng et al. |
| 11,273,301 | B2 | 3/2022 | Pfeffer et al. |
| 11,305,105 | B2 | 4/2022 | Corbett et al. |
| 11,311,712 | B2 | 4/2022 | Zeng et al. |
| 11,338,124 | B2 | 5/2022 | Pfeffer et al. |
| 11,357,967 | B2 | 6/2022 | Zeng et al. |
| 11,400,276 | B2 | 8/2022 | Chopra et al. |
| 11,497,896 | B2 | 11/2022 | Tanner et al. |
| 11,511,101 | B2 | 11/2022 | Hastie et al. |
| 11,517,736 | B2 | 12/2022 | Earles et al. |
| 11,583,659 | B2 | 2/2023 | Pfeffer et al. |
| 11,628,294 | B2 | 4/2023 | Chopra et al. |
| 11,708,833 | B2 | 7/2023 | McBride et al. |
| 11,754,075 | B2 | 9/2023 | Schuelke et al. |
| 11,786,700 | B2 | 10/2023 | Pfeffer et al. |
| 2005/0096723 | A1* | 5/2005 | Nash ...................... A61B 17/22 623/1.11 |
| 2006/0155158 | A1* | 7/2006 | Aboul-Hosn ......... A61M 60/82 600/16 |
| 2008/0114339 | A1 | 5/2008 | McBride et al. |
| 2009/0060743 | A1 | 3/2009 | McBride et al. |
| 2017/0080189 | A1 | 3/2017 | Tao et al. |
| 2017/0232169 | A1 | 8/2017 | Muller |
| 2017/0296725 | A1 | 10/2017 | Peters et al. |
| 2018/0303990 | A1 | 10/2018 | Siess et al. |
| 2018/0311423 | A1 | 11/2018 | Zeng et al. |
| 2021/0015982 | A1 | 1/2021 | Kerkhoffs et al. |
| 2021/0038785 | A1 | 2/2021 | Siess et al. |
| 2021/0077680 | A1 | 3/2021 | Tanner et al. |
| 2021/0106810 | A1 | 4/2021 | Pfeffer et al. |
| 2021/0361926 | A1 | 11/2021 | Corbett et al. |
| 2022/0134082 | A1 | 5/2022 | Pfeffer et al. |

FOREIGN PATENT DOCUMENTS

| | | | |
|---|---|---|---|
| EP | 3352808 | B1 | 9/2023 |
| JP | 2008178690 | A | 8/2008 |
| JP | 2018527129 | A | 9/2018 |
| WO | 0117581 | A2 | 3/2001 |

OTHER PUBLICATIONS

International Search Report and Written Opinion for International Application No. PCT/US2022/041232, dated Jan. 30, 2023. (18 pages).

* cited by examiner 400, 406
402
134
102, 108
404
136

400, 406
402
134
136
102, 108
404

300, 302

PERCUTANEOUS CIRCULATORY SUPPORT SYSTEM HAVING IMPROVED TORQUE AND BLOOD FLOW

CROSS-REFERENCE TO RELATED APPLICATION

The present application claims priority to Provisional Application No. 63/237,001 filed Aug. 25, 2021, which is herein incorporated by reference in its entirety.

TECHNICAL FIELD

The present disclosure relates to percutaneous circulatory support systems. More specifically, the disclosure relates to percutaneous circulatory support devices and guidewires for positioning such devices within the heart.

BACKGROUND

Percutaneous circulatory support devices such as blood pumps can provide transient support for up to approximately several weeks in patients with compromised heart function or cardiac output. Generally, the performance of such devices, more specifically blood flow and torque generation characteristics, improves by increasing the size or diameter of the impeller, motor, or other components, while also reducing device-induced hemolysis (that is, the rupture or destroying of blood cells). Such devices are typically delivered to a patient's heart using a guidewire, and the guidewire is positioned between the blood pump and the inner surface of an introducer sheath. Thus, the guidewire takes up space within the introducer sheath that could otherwise accommodate the blood pump.

SUMMARY

In an Example 1, a percutaneous circulatory support system comprises: a guidewire comprising: a distal section having a first transverse dimension; and a proximal section having a second transverse dimension, the second transverse dimension being less than the first transverse dimension; a blood pump configured to be coupled to and moved along the guidewire, the blood pump comprising: an impeller housing; a motor housing; an impeller disposed within the impeller housing, the impeller configured to cause blood to flow through the blood pump.

In an Example 2, the percutaneous circulatory support system of Example 1, wherein the impeller housing has a third transverse dimension, the motor housing has a fourth transverse dimension, and the fourth transverse dimension is less than the third transverse dimension.

In an Example 3, the percutaneous circulatory support system of Example 2, wherein the third transverse dimension is a diameter and the fourth transverse dimension is a diameter.

In an Example 4, the percutaneous circulatory support system of either of Examples 2 or 3, further comprising an introducer sheath configured to receive the guidewire and the blood pump.

In an Example 5, the percutaneous circulator support system of Example 4, wherein the introducer sheath has an inner transverse dimension, the third transverse dimension being in a range from 99.75 percent to 98.25 percent of the inner transverse dimension.

In an Example 6, the percutaneous circulator support system of Example 4, wherein the introducer sheath has an inner transverse dimension, the fourth transverse dimension being in a range from 91.25 percent to 91.75 percent of the inner transverse dimension.

In an Example 7, the percutaneous circulatory support system of any of Examples 1-6, wherein the guidewire further comprises a transition section between the proximal section and the distal section.

In an Example 8, the percutaneous circulatory support system of any of Examples 1-7, wherein the impeller housing comprises an inlet and an outlet, and the guidewire is configured to extend proximally from the outlet, through the impeller housing, and distally from the inlet.

In an Example 9, the percutaneous circulatory support system of Example 8, wherein the proximal section of the guidewire is configured to extend proximally from the outlet, through the impeller housing, and distally from the inlet.

In an Example 10, the percutaneous circulatory support system of either of Examples 8 or 9, wherein the distal section of the guidewire is configured to extend proximally from the outlet, through the impeller housing, and distally from the inlet.

In an Example 11, the percutaneous circulatory support, system of any of Examples 1-10, wherein the first transverse dimension is a diameter and the second transverse dimension is a diameter.

In an Example 12, a percutaneous circulatory support system comprises: a guidewire comprising a proximal section having a guidewire proximal section transverse dimension; a blood pump configured to be coupled to and moved along the guidewire, the blood pump comprising: an impeller assembly housing having an impeller assembly housing transverse dimension and an impeller assembly disposed within the impeller assembly housing, the impeller assembly including an impeller configured to cause blood to flow through the pump; and a motor housing coupled to the impeller housing, the motor housing having a motor housing transverse dimension; wherein:

$$d_{ih} \geq d_{mh} + 2d_{gps}; \text{ where} \qquad \text{a.}$$

$d_{ih}$ is the impeller assembly housing transverse dimension; $d_{mh}$ is the motor housing transverse dimension; and $d_{gps}$ is the guidewire proximal section transverse dimension.

In an Example 13, the percutaneous circulatory support system of Example 12, wherein the guidewire further comprises a distal section coupled to the proximal section, the distal section having a guidewire distal section transverse dimension, wherein:

$$d_{ih} \leq d_{mh} + 2d_{gds}; \text{ where} \qquad \text{a.}$$

$d_{gds}$ is the guidewire distal section transverse dimension.

In an Example 14, the percutaneous circulatory support system of either of Examples 12 or 13, further comprising an introducer sheath configured to receive the proximal section of the guidewire and the blood pump.

In an Example 15, the percutaneous circulatory support system of any of Examples 12-14, wherein the impeller assembly housing comprises an inlet and an outlet, and the guidewire is configured to extend proximally from the outlet, through the impeller assembly housing, and distally from the inlet.

In an Example 16, a percutaneous circulatory support system comprises a guidewire comprising: a distal section having a first transverse dimension; and a proximal section having a second transverse dimension, the second transverse dimension being less than the first transverse dimension; a blood pump configured to be coupled to and moved along the guidewire, the blood pump comprising: an impeller housing having a third transverse dimension; a motor housing coupled to the impeller housing, the motor housing having a fourth transverse dimension, the fourth transverse dimension being less than the third transverse dimension; an impeller disposed within the impeller housing, the impeller configured to cause blood to flow through the blood pump.

In an Example 17, the percutaneous circulatory support system of Example 16, wherein the first transverse dimension is a first diameter and the second transverse dimension is a second diameter.

In an Example 18, the percutaneous circulatory support system of Example 16, wherein the third transverse dimension is a first diameter and the fourth transverse dimension is a second diameter.

In an Example 19, the percutaneous circulatory support system of Example 16, wherein the guidewire further comprises a transition section between the proximal section and the distal section.

In an Example 20, the percutaneous circulatory support system of Example 16, further comprising an introducer sheath configured to receive the proximal section of the guidewire and the blood pump.

In an Example 21, the percutaneous circulatory support system of Example 20, wherein the introducer sheath has an inner transverse dimension, the third transverse dimension being in a range from 99.75 percent to 98.25 percent of the inner transverse dimension.

In an Example 22, the percutaneous circulatory support system of Example 16, wherein the impeller housing comprises an inlet and an outlet, and the guidewire is configured to extend proximally from the outlet, through the impeller housing, and distally from the inlet.

In an Example 23, the percutaneous circulatory support, system of Example 22, wherein the proximal section of the guidewire is configured to extend proximally from the outlet, through the impeller housing, and distally from the inlet.

In an Example 24, the percutaneous circulatory support system of Example 22, wherein the distal section of the guidewire is configured to extend proximally from the outlet, through the impeller housing, and distally from the inlet.

In an Example 25, the percutaneous circulatory support system of Example 20, wherein the introducer sheath has an inner transverse dimension, the fourth transverse dimension being in a range from 91.25 percent to 91.75 percent of the inner transverse dimension.

In an Example 26, a percutaneous circulatory support system comprises a guidewire comprising a proximal section having a guidewire proximal section transverse dimension; a blood pump configured to be coupled to and moved along the guidewire, the blood pump comprising: an impeller assembly housing having an impeller assembly housing transverse dimension and an impeller assembly disposed within the impeller assembly housing, the impeller assembly including an impeller configured to cause blood to flow through the pump; and a motor housing coupled to the impeller housing, the motor housing having a motor housing transverse dimension; wherein $$d_{ih} \geq d_{mh} + 2d_{gps}; \text{ where} \quad \text{a.}$$

$d_{ih}$ is the impeller assembly housing transverse dimension; $d_{mh}$ is the motor housing transverse dimension; and $d_{gps}$ is the guidewire proximal section transverse dimension.

In an Example 27, the percutaneous circulatory support system of Example 26, wherein the guidewire further comprises a distal section coupled to the proximal section, the distal section having a guidewire distal section transverse dimension, wherein:

$$d_{ih} \leq d_{mh} + 2d_{gds}; \text{ where} \quad \text{a.}$$

$d_{gds}$ is the guidewire distal section transverse dimension.

In an Example 28, the percutaneous circulatory support system of Example 26, further comprising an introducer sheath configured to receive the proximal section of the guidewire and the blood pump.

In an Example 29, the percutaneous circulatory support system of Example 28, wherein the introducer sheath has an inner transverse dimension, the impeller assembly housing transverse dimension being in a range from 99.75 percent to 98.25 percent of the inner transverse dimension.

In an Example 30, a method for positioning a blood pump within a subject comprises: inserting an introducer sheath at an access point in a blood vessel of the subject; inserting a guidewire into the introducer sheath, the guidewire having a distal section and a proximal section, the distal section having a first transverse dimension and the proximal section having a second transverse dimension, the second transverse dimension being less than the first transverse dimension; and advancing the blood pump through the introducer sheath and along the proximal section of the guidewire, the blood pump comprising an impeller housing having a third transverse dimension, a motor housing having a fourth transverse dimension, the fourth transverse dimension being less than the third transverse dimension, and an impeller disposed within the impeller housing and configured to cause blood to flow through the blood pump.

In an Example 31, the method of Example 30, further comprising, after advancing the blood pump through the introducer sheath and along the proximal section of the guidewire, advancing the blood pump along the distal section of the guidewire.

In an Example 32, the method of Example 30, wherein advancing the blood pump comprises extending the guidewire through an inlet and an outlet of the blood pump.

In an Example 33, the method of Example 30, wherein advancing the blood pump comprises simultaneously advancing the blood pump through the introducer sheath and along the proximal section of the guidewire.

In an Example 34, the method of Example 33, wherein advancing the blood pump further comprises, after simultaneously advancing the blood pump through the introducer sheath and along the proximal section of the guidewire, simultaneously advancing the blood pump distally from the introducer sheath and along distal section of the guidewire.

In an Example 35, the method of Example 30, wherein the introducer sheath has an inner transverse dimension, and the third transverse dimension is in a range from 99.75 percent to 98.25 percent of the inner transverse dimension.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
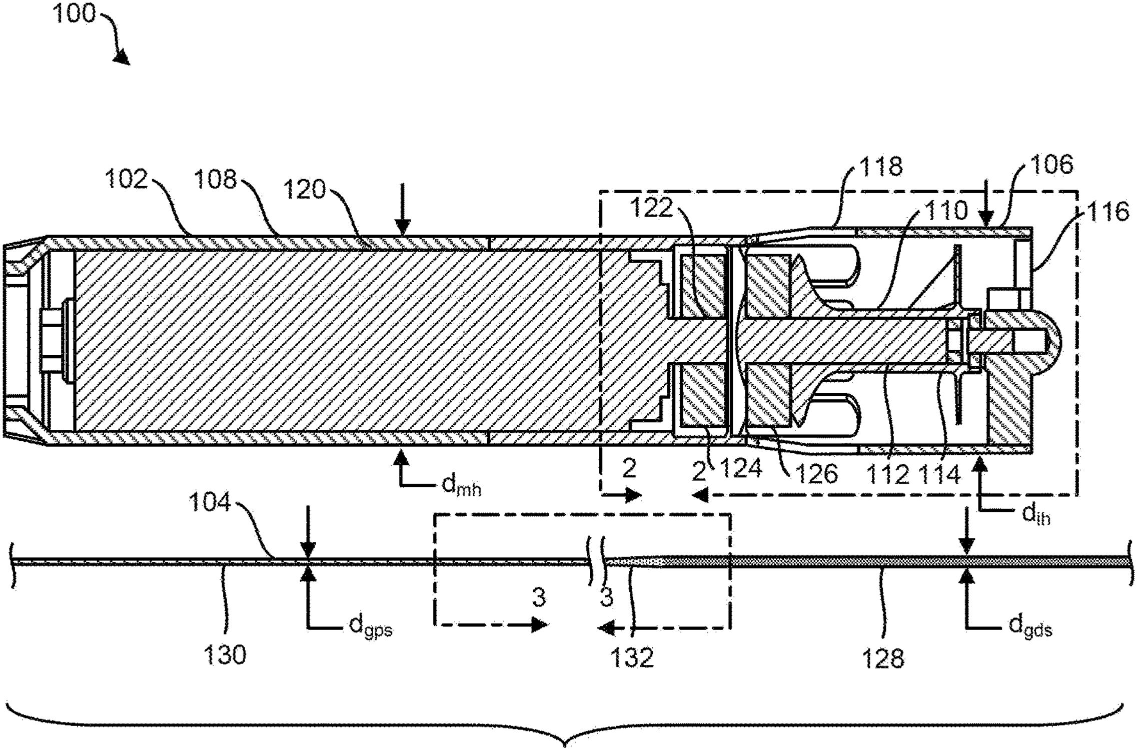
FIG. 1 is a side sectional view of several components of an illustrative percutaneous circulatory support system, in accordance with embodiments of the subject matter disclosed herein.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 depicts a side sectional view of several components of an illustrative percutaneous circulatory support system 100 in accordance with embodiments of the subject matter disclosed herein. Generally, the system 100 includes a mechanical circulatory support device 102 (also referred to herein, interchangeably, as a "blood pump"), a guidewire 104, and an introducer sheath (shown elsewhere). As described in further detail below, the guidewire 104 and the introducer sheath facilitate percutaneously delivering the blood pump 102 to a target location within a patient, such as within the patient's heart.

Figure 2:
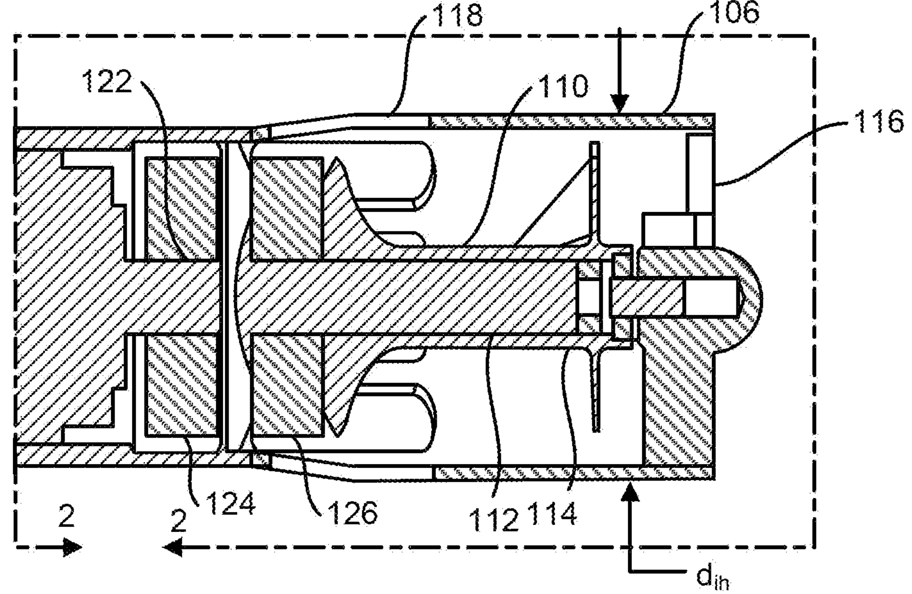
FIG. 2 is an enlarged side sectional view of a mechanical circulatory support device (also referred to herein, interchangeably, as a "blood pump") of the system and within line 2-2 of FIG. 1, in accordance with embodiments of the subject matter disclosed herein.

With continued reference to FIG. 1 and additional reference to FIG. 2, the blood pump 102 generally includes an impeller assembly housing 106 and a motor housing 108. In some embodiments, the impeller housing 106 and the motor housing 108 may be integrally or monolithically constructed. In other embodiments, the impeller assembly housing 106 and the motor housing 108 may be separate components configured to be removably or permanently coupled.

The impeller assembly housing 106 carries an impeller assembly 110 therein. The impeller assembly 110 includes an impeller shaft 112 and an impeller 114 that rotates relative to the impeller assembly housing 106 to drive blood through the blood pump 102. More specifically, the impeller 114 causes blood to flow from a blood inlet 116 formed on the impeller assembly housing 106, through the impeller assembly housing 106, and out of a blood outlet 118 formed on the impeller housing 106. In some embodiments the impeller shaft 112 and the impeller 114 may be integrated, and in other embodiments the impeller shaft 112 and the impeller 114 may be separate components. As shown in FIGS. 1 and 2, the inlet 116 and/or the outlet 118 may each include multiple apertures. In other embodiments, the inlet 116 and/or the outlet 118 may each include a single aperture. As shown in FIGS. 1 and 2, the inlet 116 may be formed on an end portion of the impeller assembly housing 106 and the outlet 118 may be formed on a side portion of the impeller assembly housing 106. In other embodiments, the inlet 116 and/or the outlet 118 may be formed on other portions of the impeller assembly housing 106. In some embodiments, the impeller assembly housing 106 may couple to a distally extending cannula (not shown), and the cannula may receive and deliver blood to the inlet 116.

With continued reference to FIGS. 1 and 2, the motor housing 108 carries a motor 120, and the motor 120 is configured to rotatably drive the impeller 114 relative to the impeller assembly housing 106. In the illustrated embodiment, the motor 120 rotates a drive shaft 122, which is coupled to a driving magnet 124. Rotation of the driving magnet 124 causes rotation of a driven magnet 126, which is connected to the impeller assembly 110. More specifically, in embodiments incorporating the impeller shaft 112, the impeller shaft 112 and the impeller 114 are configured to rotate with the driven magnet 126. In other embodiments, the motor 120 may couple to the impeller assembly 110 via other components.

In some embodiments, a controller (not shown) may be operably coupled to the motor 120 and configured to control the motor 120. In some embodiments, the controller may be disposed within the motor housing 108. In other embodiments, the controller may be disposed outside of the motor housing 108 (for example, in a catheter handle, an independent housing, etc.). In some embodiments, the controller may include multiple components, one or more of which may be disposed within the motor housing 108. According to embodiments, the controller may be, may include, or may be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. Although the controller is referred to herein in the singular, the controller may be implemented in multiple instances, distributed across multiple computing devices, instantiated within multiple virtual machines, and/or the like. In other embodiments, the motor 120 may be controlled in other manners.

With further reference to FIGS. 1 and 2, the system 100 provides improved torque and blood flow compared to conventional systems and may reduce device-induced hemolysis. Generally, this improved performance is facilitated by the relative dimensions of different sections of the blood pump 102 and the guidewire 104. More specifically, the guidewire 104 includes a distal section 128 having a first, relatively large transverse dimension $d_{gds}$ and a proximal section 130 having a second, relatively small transverse dimension $d_{gps}$ (as used herein, a "transverse dimension" is understood to refer to a diameter for a circular component or a largest width dimension for a component having a non-circular cross section). Stated another way, the second transverse dimension $d_{gps}$ of the guidewire 104 is less than the first transverse dimension $d_{gds}$ of the guidewire 104. The first transverse dimension $d_{gds}$ of the guidewire 104 may be similar to the transverse dimension of a conventional guidewire 104, to facilitate advancement through the vasculature of a patient, and the second transverse dimension $d_{gps}$ of the guidewire 104 may be less than the transverse dimension of a conventional guidewire, for reasons that will be more apparent from the following paragraphs. In some embodiments, the first transverse dimension $d_{gds}$ and/or the second transverse dimension $d_{gps}$ are diameters. In some embodiments, the first transverse dimension $d_{gds}$ of the guidewire 104 may be in a range of 0.014 to 0.035 inches. In some embodiments, the second transverse dimension $d_{gps}$ of the guidewire 104 may be in a range of 0.006 to 0.1018 inches.

The impeller assembly housing 106 includes a third, relatively large transverse dimension $d_{ih}$ and the motor housing 108 includes a fourth, relatively small transverse dimension $d_{mh}$. In some embodiments, the fourth transverse dimension $d_{mh}$ of the blood pump 102 is less than the third transverse dimension $d_{ih}$ of the blood pump 102. In other embodiments, the fourth transverse dimension $d_{mh}$ of the blood pump 102 may be similar to or the same as the third transverse dimension $d_{ih}$ of the blood pump 102. The third transverse dimension $d_{ih}$ of the blood pump 102 may be larger than that of a conventional blood pump, and the fourth transverse dimension $d_{mh}$ of the blood pump 102 may be similar to or larger than that of a conventional blood pump, for reasons that will be more apparent from the following paragraphs. In some embodiments, the third transverse dimension $d_{ih}$ and/or the fourth transverse dimension $d_{mh}$ are diameters. In some embodiments, the third transverse dimension $d_{ih}$ of the blood pump 102 may be in a range of 0.205 to 0.211 inches, or a range of 0.189 to 0.195 inches. In some embodiments, the fourth transverse dimension $d_{mh}$ of the blood pump 102 may be in a range of 0.1805 to 0.1865 inches, or a range of 0.189 to 0.195 inches.

Figure 3:
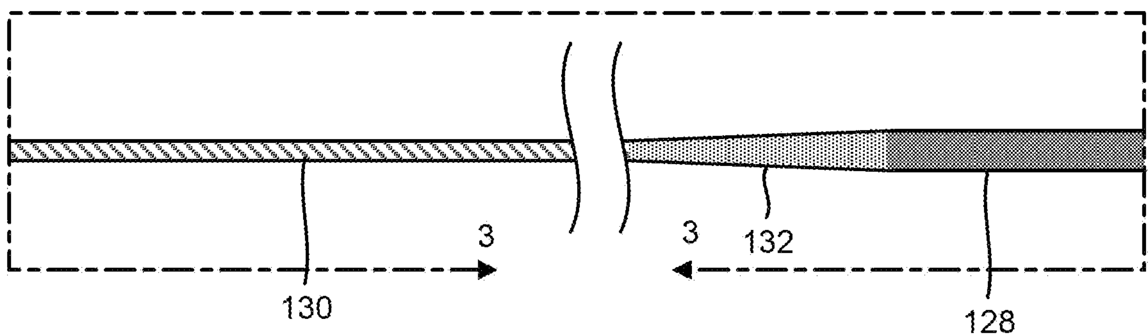
FIG. 3 is an enlarged side sectional view of a guidewire of the system and within line 2-2 of FIG. 1, in accordance with embodiments of the subject matter disclosed herein.

With reference now to FIGS. 1 and 3, in some embodiments the guidewire 104 includes a transition section 132 that couples the distal section 128 to the proximal section 130. The transition section 132 is tapered to match the dimensions of the proximal section 130 and distal section 128, resulting in an overall tapered diameter profile for guidewire 104. In other embodiments, the transition section 132 may be omitted. In some embodiments, the dimensions of the proximal section 130, the transition section 132, and the distal section 128 may be uniform along their length; however, in other embodiments, the dimensions of the proximal section 130, the transition section 132, and/or the distal section 128 may be non-uniform along their length.

The guidewire 104 may be formed through a variety of methods, including for example, centerless grinding, stamping or rolling processing, a combination of both, or by other shape forming methods. In some embodiments, the guidewire 104 may include a coating (not shown) that facilitates trackability within patient vasculature and reduces friction while advancing the blood pump 102 over the guidewire 104. Such coatings may include PTFE, polymer coatings, or ceramic coatings through chemical vapor deposition processes such as atomic layer deposition. Incorporation of a smaller dimensioned proximal section 130 of the guidewire 104 may also reduce the likelihood of stripping the coating on the edges of the windows of the pump outlet 118 (see FIGS. 1 and 2) by urging the guidewire 104 to exit from the windows of the pump outlet 118 close to parallel with the outer edge of the motor housing 108.

As described briefly above, the system 100 may also include an introducer sheath (shown elsewhere). Generally, the introducer sheath has a lumen with an inner diameter and an outer diameter. The introducer sheath may be constructed of various appropriate materials, such as silicone, Vestamid®, polyethylene, low density polyethylene, high density polyethylene polyurethane, thermoplastic rubber, polypropylene, Pebax®, or other medical grade synthetics or plastics. Metallics such as stainless-steel and nitinol may be used to provide the introducer sheath with structural integrity, flexibility, expansion/collapse properties, or other such features. In other embodiments, the guidewire 104 and blood pump 102 may be delivered without the use of an introducer sheath. Instead, the guidewire 104 and the blood pump 102 may be delivered via a graft anastomized to a blood vessel, forming a wye-connection with the anatomy. In some embodiments, the introducer sheath may have an inner transverse dimension (more specifically, an inner diameter) in a range of 0.209 to 0.214 inches.

Figure 4:
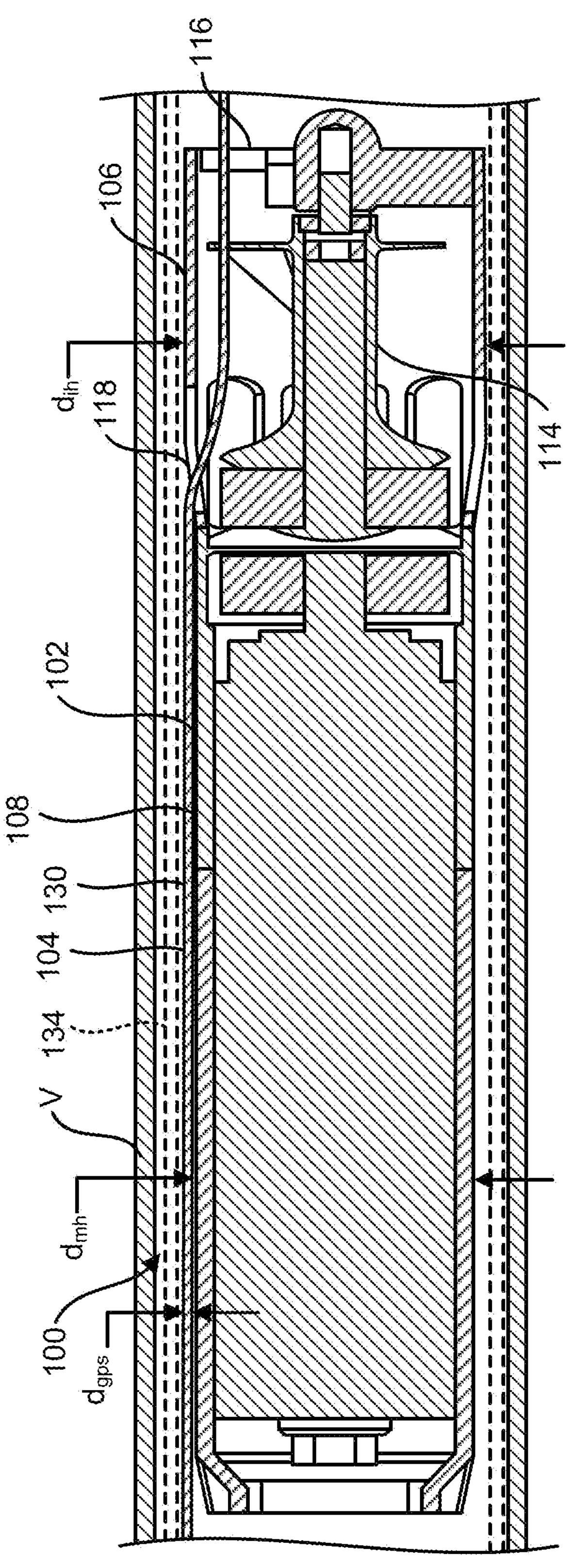
FIG. 4 is a side sectional view of the system of FIG. 1 upon initial insertion into a blood vessel of a patient, in accordance with embodiments of the subject matter disclosed herein.

FIG. 4 illustrates the system 100 upon initial insertion into a blood vessel V, such as the femoral artery of a patient. More specifically, the introducer sheath 134 is inserted into the blood vessel V, and the guidewire 104 is inserted through the introducer sheath 134 such that the proximal section 130 is disposed within the introducer sheath 134 and the distal section 128 (shown elsewhere) is disposed distally from the introducer sheath 134. The blood pump 102 is also initially positioned within the introducer sheath 134 and movably coupled to the guidewire 104. More specifically, the proximal section 130 of the guidewire 104 extends distally from the pump inlet 116, through the impeller assembly housing 106, and proximally from the pump outlet 118.

Figure 5:
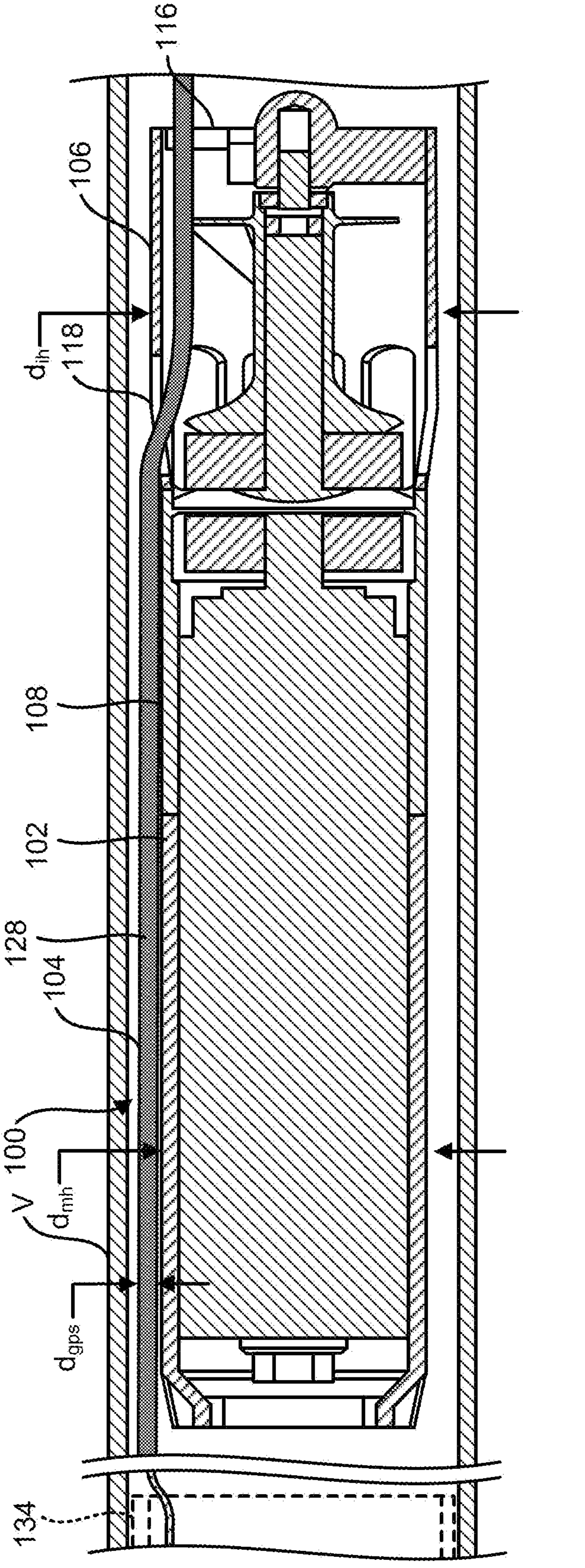
FIG. 5 is a side sectional view of the system of FIG. 1 in the blood vessel of the patient and upon distal advancement from the position illustrated in FIG. 4, in accordance with embodiments of the subject matter disclosed herein.

FIG. 5 illustrates the system 100 upon distal advancement from the position illustrated in FIG. 4. More specifically, the distal section 128 of the guidewire 104 and the blood pump 102 are located in the blood vessel V distally from the introducer sheath 134. The distal section 128 of the guidewire 104 extends distally from the pump inlet 116, through the impeller assembly housing 106, and proximally from the pump outlet 118.

FIGS. 4 and 5 also facilitate further explanation of the advantages provided by the dimensions of the sections of the blood pump 102 and the guidewire 104. As shown in FIG. 4, the proximal section 130 of the guidewire 104 provides for additional clearance within the introducer sheath 134 due to its relatively small transverse dimension $d_{gps}$. As a result, the proximal section 130 of the guidewire 104 permits the blood pump 102 to move through the introducer sheath 134 while also permitting the blood pump 102 to be relatively large compared to conventional blood pumps. For example, one or more components of the blood pump 102 proximal to the outlet 118, such as the motor 120, the driving magnet 124, and/or the driven magnet 126 (all shown in FIG. 1) may have relatively large sizes compared those of conventional blood pumps. As another example, one or more components distal to the outlet 118, such as the impeller assembly housing 106 and the impeller 114, may have relatively large sizes compared those of conventional blood pumps. As a specific example, the impeller assembly housing 106 may have a relatively large transverse dimension dh, as described above. Providing relatively large dimensions for these components of the blood pump 102 can permit more torque to be generated by the motor 120, the driving magnet 124, and/or driven magnet 126, or for the impeller 114 to provide increased blood flow and/or reduced hemolysis. For example, by increasing the size of certain components, such as the impeller 114, the blood pump 102 can achieve greater blood flow rates at lower rotational speeds of the impeller 114, reducing the likelihood of hemolysis. Such configurations also may allow for the rigid length of the blood pump 102 to be relatively shorter as compared with conventional blood pumps, which facilitates navigating the patient's vasculature with the blood pump 102.

Additionally, and in contrast to conventional blood pumps, the transverse dimension do of the impeller assembly housing 106 may be only slightly less than the internal transverse dimension of the introducer sheath 134 (for example, the inner diameter of the introducer sheath 134). More specifically, the transverse dimension $d_{ih}$ of the impeller assembly housing 106 may be in a range from 99.75 percent to 98.25 percent of the internal transverse dimension of the introducer sheath 134, a range from 99.5 percent to 98.5 percent, or a range from 99.25 percent to 98.75 percent. Similarly, and unlike conventional blood pumps, the transverse dimension $d_{ih}$ of the impeller assembly housing 106 may be similar to the sum of the transverse dimension $d_{mh}$ of the motor housing 108 and the transverse dimension $d_{gps}$ of the proximal section 130 of guidewire 104. More specifically, the transverse dimension $d_{ih}$ of the impeller assembly housing 106 may be as shown in Equation 1:

$$d_{ih} \geq d_{mh} + 2d_{gps} \quad (1)$$

Similarly, and in contrast to conventional blood pumps, the transverse dimension $d_m$h of the motor housing 108 may be only slightly less than the internal transverse dimension of the introducer sheath 134. More specifically, the transverse dimension $d_{mh}$ of the motor housing 108 may be in a range from 90.75 percent to 92.25 percent of the internal transverse dimension of the introducer sheath 134, a range from 91.00 percent to 92.00 percent, or a range from 91.25 percent to 91.75 percent.

Turning now to FIG. 5, the transverse dimension $d_{gds}$ of the distal section 128 of the guidewire 104 may be larger than the transverse dimension $d_{gps}$ of the proximal section 130, and in some embodiments similar to the transverse dimension of a conventional guidewire, because (1) the distal section 128 is configured to be disposed distally from the introducer sheath 134, and as a result the distal section 128 would not cause interference as the blood pump 102 moves through the introducer sheath 134; and (2) to facilitate advancement through the vasculature of a patient. In some embodiments, the transverse dimension $d_{gds}$ of the distal section 128 may relate to the transverse dimension $d_{ih}$ of the impeller assembly housing 106 and the transverse dimension $d_{mh}$ of the motor housing 108 as shown in Equation 2:

$$d_{ih} \leq d_{mh} + 2d_{gds} \quad (2)$$

The illustrative system 100 shown in FIGS. 1-5 is not intended to suggest any limitation as to the scope of use or functionality of embodiments of the present disclosure. The illustrative system 100 also should not be interpreted as having any dependency or requirement related to any single component or combination of components illustrated therein. Additionally, various components depicted in FIGS. 1-5 may be, in some embodiments, integrated with various ones of the other components depicted therein (and/or components not illustrated), all of which are considered to be within the ambit of the present disclosure.

Figures 6A, 6B, 6C:
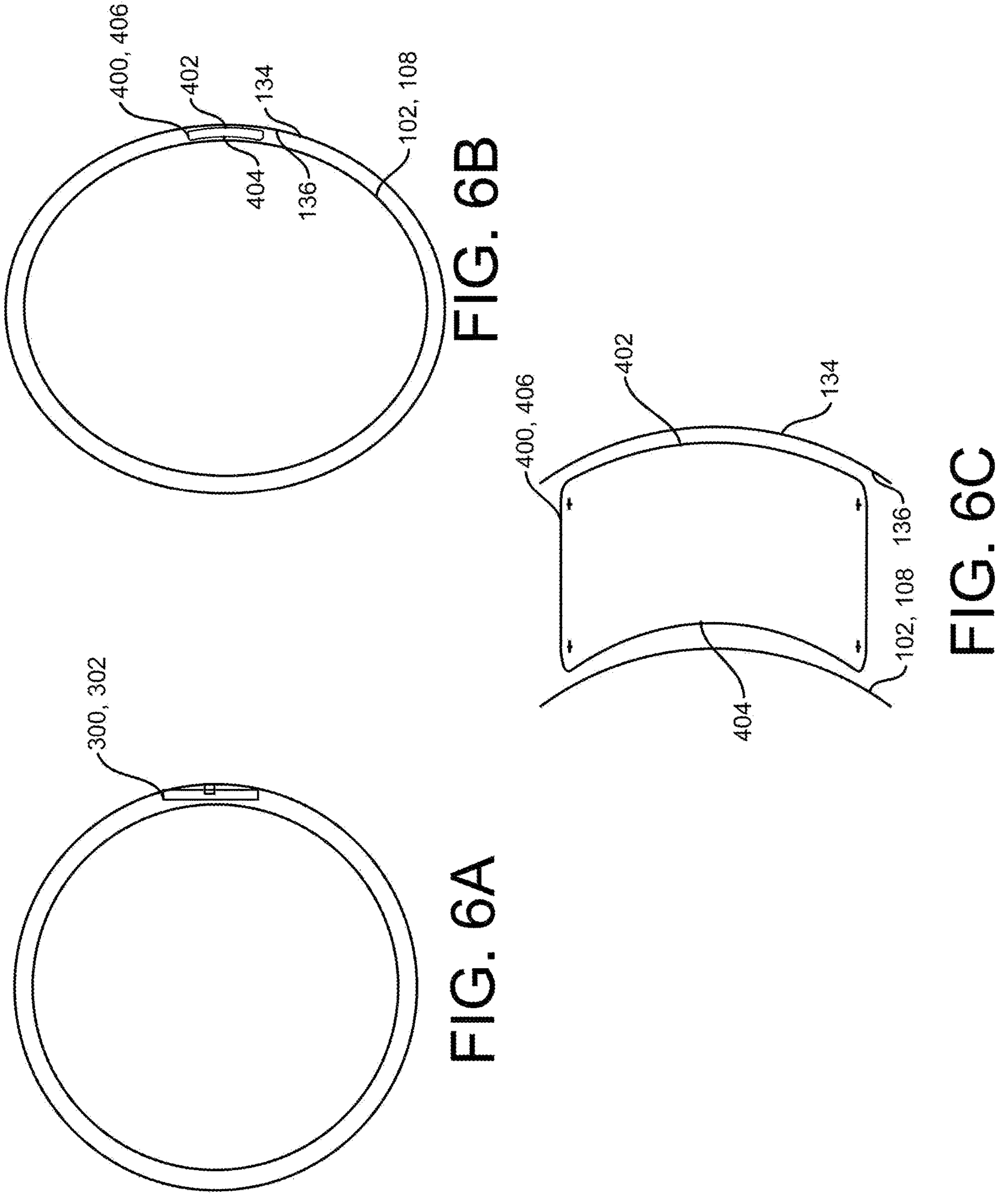
FIG. 6A is a cross-sectional view of another illustrative guidewire, in accordance with embodiments of the subject matter disclosed herein.
FIG. 6B is a cross-sectional view of another illustrative guidewire, in accordance with embodiments of the subject matter disclosed herein.
FIG. 6C is a cross-sectional view of yet another illustrative guidewire, in accordance with embodiments of the subject matter disclosed herein.

Systems according to the present disclosure may be modified in various other forms. For example, guidewires according to the present disclosure may be modified in various other forms. More specifically, the distal section of a guidewire could include one or more flexible portions to reduce or eliminate potential trauma to the patient's vasculature, for example, during insertion. As another example, the proximal section of a guidewire may have a different cross-sectional shape than the distal section of a guidewire and/or the transition section of a guidewire. FIGS. 6A-6C illustrate several embodiments such guidewires, which may be used in the system 100 instead of the guidewire 104. In a similar manner to the guidewire 104, however, the guidewires illustrated in FIGS. 6A-6C include relatively narrow proximal sections to provide more space in the introducer sheath 134 for the blood pump 102 than if the proximal sections were the same dimension and/or shape as the distal sections of the guidewires, and/or compared to conventional guidewires.

FIG. 6A illustrates another embodiment of a guidewire 300 according to the present disclosure. The guidewire 300 has a relatively flat shape. More specifically, a proximal section 302, a transition section (not shown), and/or a distal section (not shown) may have a relatively flat shape. In some embodiments, the distal section may have a transverse dimension (more specifically, a thickness) in a range of 0.014 to 0.035 inches and the proximal section 302 may have a transverse dimension (more specifically, a thickness) in a range of 0.003 to 0.014 inches.

FIGS. 6B and 6C illustrates another embodiment of a guidewire 400 according to the present disclosure. The guidewire 400 has a generally curved profile. More specifically, the guidewire 400 includes an exterior surface 402 and an interior surface 404 that is the same as, or similar to, the inner surface 136 of the introducer sheath 134 and the outer surface of the motor housing 108 of the blood pump 102 (both shown in FIG. 1), respectively. In some embodiments, the proximal section 406, a transition section (not shown), and/or a distal section (not shown) may have a curved profile. In some embodiments and as shown in FIG. 6C, the curved profile has radiused corners. These radiused corners help inhibit the guidewire from scraping the introducer sheath 134 and/or the blood pump 102.

Figure 7:
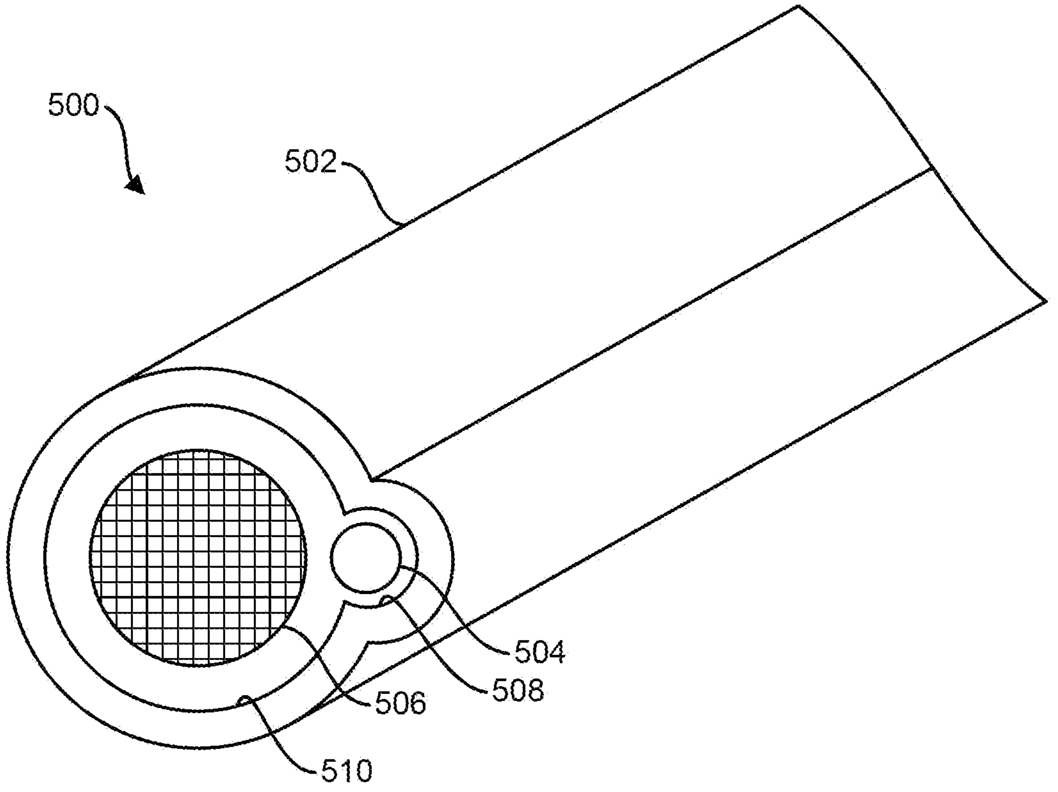
FIG. 7 is a perspective sectional view of another illustrative percutaneous circulatory support system, in accordance with embodiments of the subject matter disclosed herein.

FIG. 7 illustrates another an illustrative percutaneous circulatory support system 500 in accordance with embodiments of the subject matter disclosed herein. In the illustrated embodiment, the system 500 includes an introducer sheath 502, a guidewire 504, and a blood pump 506. The blood pump 506 may be the same as the blood pump 102 described above, or the blood pump 506 may be a conventional blood pump. The guidewire 504 may be the same as any of the guidewires described above, or the guidewire 504 may be a conventional guidewire. The introducer sheath 502 includes separate lumens for the guidewire 504 and the blood pump 506. More specifically, the introducer sheath 502 includes a guidewire lumen 508 that receives the guidewire 504 and a blood pump lumen 510 that receives the blood pump 506. The guidewire lumen 508 provides a relatively large amount of space within the introducer sheath 502 for the blood pump 506, because the guidewire 504 does not occupy space between the blood pump 506 and introducer sheath 502 within the blood pump lumen 510. In addition, the guidewire 504 does not contact the blood pump 506. Because the guidewire 504 does not occupy space within blood pump lumen 510, one or more components of the blood pump, such as the magnets, motor, impeller assembly housing, impeller assembly, may have relatively large dimensions to provide one or more of the advantages described above. In some embodiments, the guidewire lumen 508 may be permanently or detachably coupled to the introducer sheath 502. In other embodiments, the guidewire lumen 508 can be separate from the introducer sheath 502. The guidewire lumen 508 and introducer sheath 502 may be coupled to each other when ready for use.

The illustrative system shown in FIG. 7 is not intended to suggest any limitation as to the scope of use or functionality of embodiments of the present disclosure. The illustrative system also should not be interpreted as having any dependency or requirement related to any single component or combination of components illustrated therein. Additionally, various components depicted in FIG. 7 may be, in some embodiments, integrated with various ones of the other components depicted therein (and/or components not illustrated), all of which are considered to be within the ambit of the present disclosure.

Figure 8:
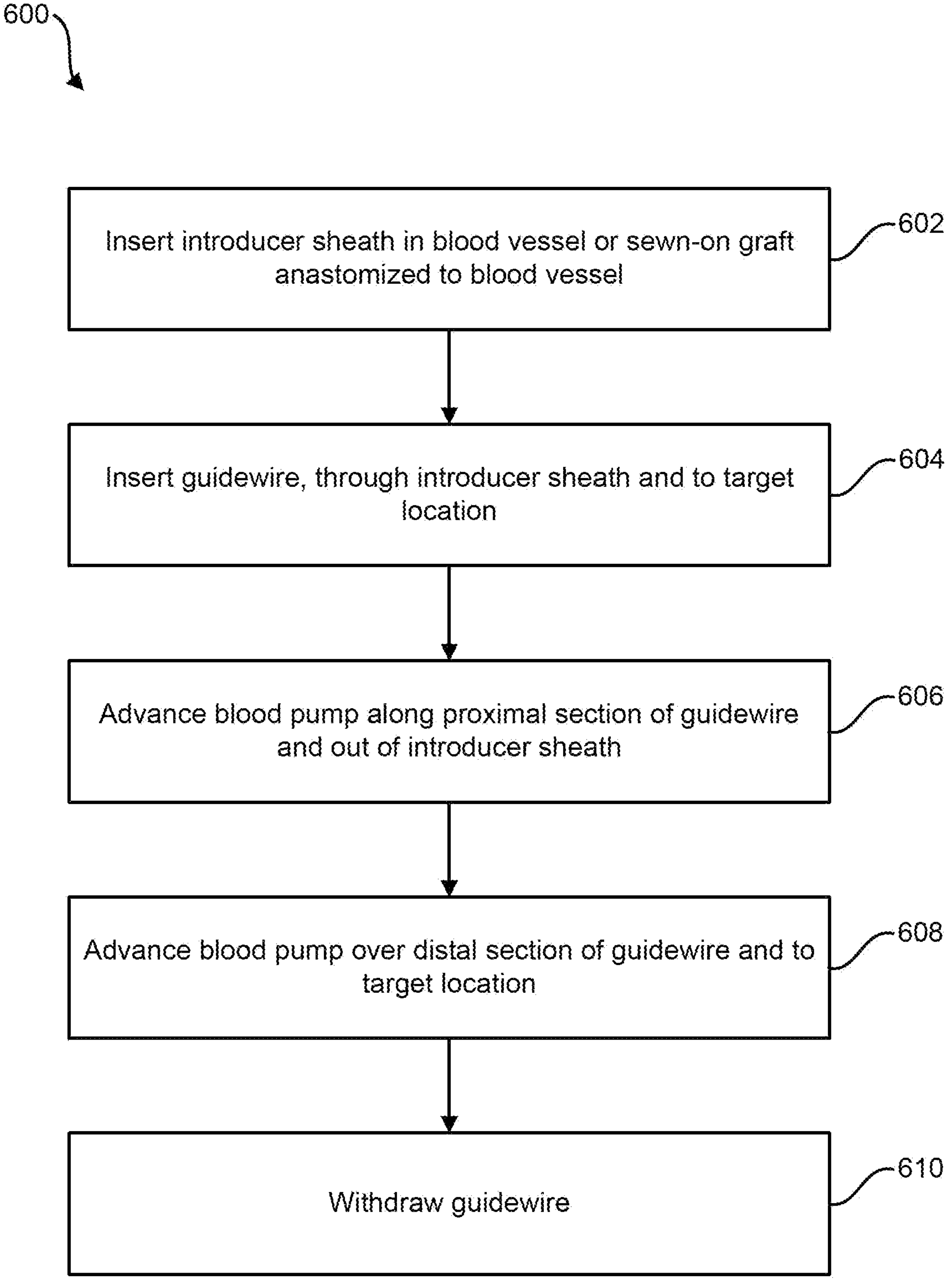
FIG. 8 is a flow diagram of an illustrative method for using a percutaneous circulatory support system and delivering a blood pump to a patient's heart, in accordance with embodiments of the subject matter disclosed herein.

FIG. 8 illustrates a flow diagram of an exemplary method 600 for using a percutaneous circulatory support system and delivering a blood pump to a patient's heart, in accordance with embodiments of the subject matter disclosed herein. The method 600 describes features of the system 100, although it is understood that any of the systems contemplated herein could be used in a similar manner. At step 602, a physician inserts the introducer sheath 134 into a blood vessel of a patient, such as the femoral artery of the patient, or places a sewn-on graft anastomized to a blood vessel that forms a wye-connection with the blood vessel. Next, the physician may insert a guide catheter (not shown) through the introducer sheath 134 to facilitate passing the guidewire 104 through the patient's vasculature. Alternatively, the guidewire 104 may be delivered through the introducer sheath 134 without the guide catheter. At step 604, the physician inserts the guidewire 104 through introducer sheath 134 and advances the guidewire 104 through the blood vessel such that the distal tip of the guidewire 104 is located in a target location within the patient, such as the left ventricle of the heart. Outside of the patient's body, the physician positions the blood pump 102 on the proximal section 130 of the guidewire 104. More specifically, the physician inserts the proximal end of the guidewire 104 into the blood inlet 116 and advances the proximal section 130 of the guidewire 104 through the impeller assembly housing 160 until the proximal section 130 emerges from the outlet 118. As a result, the physician positions the blood pump 102 such that the proximal section 130 of the guidewire 104 extends proximally from the outlet 118, through the impeller assembly housing 106, and distally from the inlet 116. At step 606, the physician advances the blood pump 102 over the proximal section 130 of the guidewire 104 and into and through the introducer sheath 134. After distally exiting the introducer sheath 134 and at step 608, the physician advances the blood pump 102 over the transition section 132 and the distal section 128 of the guidewire 104 until the blood pump 102 reaches the target location. For example, the physician may advance the blood pump 102 such that the cannula (not shown) coupled to the impeller assembly housing 106 is positioned in the left ventricle and the outlet 118 is positioned proximal of the aortic valve, for example, in the aorta. At step 610, the physician withdraws the guidewire 104 from the patient.

The illustrative method shown in FIG. 8 is not intended to suggest any limitation as to the scope of use or functionality of embodiments of the present disclosure. The illustrative method also should not be interpreted as having any dependency or requirement related to any single step or combination of steps illustrated therein.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A percutaneous circulatory support system, comprising:

a guidewire comprising:

a distal section having a first transverse dimension; and a proximal section having a second transverse dimension, the second transverse dimension being less than the first transverse dimension;

a blood pump configured to be coupled to and moved along the guidewire to a target location within a patient, the blood pump comprising:

an impeller housing having a third transverse dimension;

a motor housing coupled to the impeller housing, the motor housing having a fourth transverse dimension, the fourth transverse dimension being less than the third transverse dimension;

an impeller disposed within the impeller housing, the impeller configured to rotate relative to the impeller housing to cause blood to flow through the impeller housing of the blood pump to function as a circulatory support device when positioned at the target location; and a motor disposed within the motor housing and configured to rotatably drive the impeller.

2. The percutaneous circulatory support system of claim 1, wherein the first transverse dimension is a first diameter and the second transverse dimension is a second diameter.

3. The percutaneous circulatory support system of claim 1, wherein the third transverse dimension is a first diameter and the fourth transverse dimension is a second diameter.

4. The percutaneous circulatory support system of claim 1, wherein the guidewire further comprises a transition section between the proximal section and the distal section.

5. The percutaneous circulatory support system of claim 1, further comprising an introducer sheath configured to receive the proximal section of the guidewire and the blood pump.

6. The percutaneous circulatory support system of claim 5, wherein the introducer sheath has an inner transverse dimension, the third transverse dimension being in a range from 99.75 percent to 98.25 percent of the inner transverse dimension.

7. The percutaneous circulatory support system of claim 5, wherein the introducer sheath has an inner transverse dimension, the fourth transverse dimension being in a range from 91.25 percent to 91.75 percent of the inner transverse dimension.

8. The percutaneous circulatory support system of claim 1, wherein the impeller housing comprises an inlet and an outlet, and the guidewire is configured to extend proximally from the outlet, through the impeller housing, and distally from the inlet.

9. The percutaneous circulatory support system of claim 8, wherein the proximal section of the guidewire is configured to extend proximally from the outlet, through the impeller housing, and distally from the inlet.

10. The percutaneous circulatory support system of claim 8, wherein the distal section of the guidewire is configured to extend proximally from the outlet, through the impeller housing, and distally from the inlet.

11. A percutaneous circulatory support system, comprising:

a guidewire comprising a proximal section having a guidewire proximal section transverse dimension;

a blood pump configured to be coupled to and moved along the guidewire to a target location within a patient, the blood pump comprising:

an impeller assembly housing having an impeller assembly housing transverse dimension and an impeller assembly disposed within the impeller assembly housing, the impeller assembly including an impeller configured to cause blood to flow through the pump as a circulatory support device when positioned at the target location; and a motor housing coupled to the impeller housing, the motor housing having a motor housing transverse dimension, the motor housing having a motor disposed therein and configured to rotatably drive the impeller;

wherein:

$$d_{ih} \geq d_{mh} + 2d_{gps}; \text{ where}$$

$d_{ih}$ is the impeller assembly housing transverse dimension;

$d_{mh}$ is the motor housing transverse dimension; and $d_{gps}$ is the guidewire proximal section transverse dimension.

12. The percutaneous circulatory support system of claim 11, wherein the guidewire further comprises a distal section coupled to the proximal section, the distal section having a guidewire distal section transverse dimension, wherein:

$$d_{ih} \leq d_{mh} + 2d_{gds}; \text{ where}$$

$d_{gds}$ is the guidewire distal section transverse dimension.

13. The percutaneous circulatory support system of claim 11, further comprising an introducer sheath configured to receive the proximal section of the guidewire and the blood pump.

14. The percutaneous circulatory support system of claim 13, wherein the introducer sheath has an inner transverse dimension, the impeller assembly housing transverse dimension being in a range from 99.75 percent to 98.25 percent of the inner transverse dimension.

* * * * *